United States Patent [19]

Takahashi et al.

[11] Patent Number: 5,224,492

[45] Date of Patent: Jul. 6, 1993

[54] THERMOTHERAPY APPARATUS

[75] Inventors: Noriyuki Takahashi, Ibaraki; Tamaki Sakamoto, Kyoto; Jun Shimoyama, Uji; Eiji Kasai, Nagaokakyo; Makoto Saito, Ichikawa; Jin-ichi Matsuda, Nagaoka; Kazuo Kato, Niigata, all of Japan

[73] Assignee: Omron Corporation, Kyoto, Japan

[21] Appl. No.: 713,358

[22] Filed: Jun. 11, 1991

[30] Foreign Application Priority Data

Jun. 13, 1990 [JP] Japan .................. 2-154484
Jun. 13, 1990 [JP] Japan .................. 2-154485
Oct. 17, 1990 [JP] Japan .................. 2-279984

[51] Int. Cl.$^5$ .............................. A61N 1/00
[52] U.S. Cl. .................... 128/804; 128/399; 128/400; 128/401; 600/10
[58] Field of Search ............ 128/804, 399, 400, 401, 128/653.1, 736; 600/9, 10; 606/27, 31, 32, 33, 34

[56] References Cited

U.S. PATENT DOCUMENTS

| | | | |
|---|---|---|---|
| 4,397,314 | 8/1983 | Vaguine | 128/401 |
| 4,407,292 | 10/1983 | Edrich | 128/653.1 |
| 4,638,436 | 1/1987 | Badger et al. | 128/804 |
| 4,669,475 | 6/1987 | Turner | 128/399 |
| 4,744,372 | 5/1988 | Kikuchi et al. | 128/400 |
| 4,798,215 | 1/1989 | Turner | 128/736 |
| 4,800,899 | 1/1989 | Elliott | 128/736 |
| 4,869,247 | 9/1989 | Howard, III et al. | 606/27 |
| 4,961,422 | 10/1990 | Marchosky et al. | 128/399 |
| 5,046,495 | 9/1991 | Takahashi et al. | 128/400 |
| 5,056,531 | 10/1991 | Shimoyama | 128/400 |

FOREIGN PATENT DOCUMENTS 0170416 2/1986 European Pat. Off. ........... 128/399
1-254177 10/1989 Japan .

OTHER PUBLICATIONS

Ivan A. Brezouich, PhD et al., "A Practical System for Clinical Radiofrequency Hyperthermia", Int. J. Radiation Oncology, Biol. Phys., vol. 70, No. 3, pp. 423–430, Mar. 81.

LeVeen, MD et al, "Tumor Eradication by Radiofrequency Therapy", JAMA, vol. 235, No. 20, pp. 2198–2200, May 17, 1976.

Primary Examiner—Lee S. Cohen
Assistant Examiner—Brian L. Casler
Attorney, Agent, or Firm—Fish & Richardson

[57] ABSTRACT

In a CT image of a living body, contours of internal organs thereof are discriminated. Parameters are beforehand stored in a memory for a plurality of internal organs of the living body. Applicators are attached onto the living body and then a high frequency power is applied to electrodes disposed therein so as to heat an internal portion of the body. Based on an intensity of an electric field generated in the body due to the applied power and the parameters stored in the memory, a temperature distribution on the CT image is estimated. To retain an estimated temperature of an objective tumor at a predetermined target temperature, the high frequency power and the cooling water in the applicators are controlled. In the estimation of the temperature distribution, the parameters of the living body are repeatedly corrected to minimize a discrepancy between a temperature measured at a preset position and an estimated temperature associated therewith.

24 Claims, 18 Drawing Sheets

Fig. 3

| TEXTURE OR VISCUS NAME | $\varepsilon_r$ SPECIFIC DIELECTRIC CONSTANT | $\sigma$ (℧/m) CONDUCTIVITY | $k$ (W/m°C) HEAT TRANSFER COEFFICIENT | $\rho$ (kg/m³) VOLUME DENSITY | $c$ (J/kg°C) SPECIFIC HEAT | $F$ (m³/kgs) BLOOD FLOW RATE |
|---|---|---|---|---|---|---|
| WATER | | | | | | |
| FAT | | | | | | |
| MUSCLE | | | | | | |
| SKIN | | | | | | |
| BLOOD | | | | | | |
| --- | --- | --- | --- | --- | --- | --- | ized to achieve control of the temperature to be applied to the living body.

THERMOTHERAPY APPARATUS

BACKGROUND OF THE INVENTION

1. Field of the Invention

The present invention relates to a thermotherapy apparatus for use in thermotherapy associated with the phenomenon of hyperthermia, and in particular, to a thermotherapeutic apparatus applied to a living body in which a distribution of temperature in the organism is estimated to achieve control of the temperature to be applied to the living body.

In addition, the present invention relates to a thermotherapy apparatus applied to a living body in which a distribution of temperature in the organism is estimated to develop a thermotherapy schedule support function facilitating a thermotherapy scheduling job.

Moreover, the present invention relates to a thermotherapy schedule support apparatus helping the user easily achieve the thermotherapy scheduling process.

2. Description of Related Art

A thermotherapy apparatus for use in a thermotherapy is constituted in general of a pair of applicators, a high frequency generator, a thermostatic liquid circulator, and a temperature measuring unit. Each of the applicators includes an electrode and and a bolus or a liquid bag in which the electrode is enclosed. The high frequency generator produces and applies a high frequency voltage between the electrodes. On the other hand, in each of the boluses, a thermostatic liquid is circulated by the thermostatic liquid circulating unit. The applicators are attached onto a living body to enclose a portion of the organism therebetween such that when the high frequency voltage is applied between the electrodes of the applicators, the body sandwiched between the electrodes is dielectrically heated. The boluses are tightly fixed onto surfaces of the organism (or on an inner surface of a cavity of the body) to lower the temperature thereof.

In operation, a temperature sensor is inserted into the living body such that a first end portion thereof is placed in a tumor of the body. The sensor senses a temperature at the end portion to produce an output signal representing the temperature and then delivers the signal to the temperature measuring unit. Based on the received temperature signal, the unit conducts the measurement of the tumor temperature. The high frequency power applied to the applicator is controlled to retain the measured temperature in a certain range of temperature (for example, from 42.5° C. to 43.0° C.). When the tumor of the organism is kept in this temperature range and the heating condition is kept unchanged for a predetermined period of time, the tumor portion will possibly be destroyed to necrosis.

In the conventional thermotherapy apparatus, the high frequency power is controlled depending on the temperature sensed at "a point" of the first end of the temperature sensor. Since the electrode of the applicator has a diameter of several centimeters to several tens of centimeters and the high frequency power is emitted from an area or a surface, it is necessary to measure the distribution of temperature in a portion of the body in a two-dimensional or three-dimensional manner. Furthermore, personal characteristics such as the contour of the body and the thickness of a fatty layer vary among the patients undergoing thermotherapy.

In consequence, the apparatus for use in the thermotheraphy of conventional technology may possibly produce a hot spot at an unexpected position in some cases, which frequently leads to an accident in that portions of the living body of the patient are burnt.

Moreover, the patients usually feel pain when the temperature sensor is inserted into the body of the patient; furthermore, the inserting point may cause the patients to catch an infectious disease.

SUMMARY OF THE INVENTION

It is therefore an object of the present invention to provide a thermotherapy apparatus applied to thermotherapy of a living body in which the distribution of temperature in the organism is estimated based on an estimated temperature distribution, and control of the high frequency power is produced so as to adjust the temperature to be applied to the living body.

In addition, another object of the present invention is to provide a thermotherapy apparatus or a thermotherapy schedule support apparatus for use in a thermotherapy treatment of the living body in which a distribution of temperature in the organism is estimated to develop a thermotherapy schedule support function, facilitating the generating of a comprehensive thermotherapy schedule so as to conduct efficient treatment without danger.

According to the present invention, there is provided a thermotherapy apparatus including applicators each having an electrode for applying a high frequency power to a living body, means for generating the high frequency power to be applied between the electrodes, means for measuring the temperature of a predetermined position of the organism, and means for setting a heating condition to heat the organism, comprising means for acquiring an image of the living body generated by computer tomography (CT), organism parameter store means for storing parameters of textures and/or internal organs of the living body, and temperature distribution estimate means for repeatedly modifying values of the organism parameters to minimize the temperature discrepancy between the temperature of the predetermined position of the living body repeatedly measured by the temperature measure means and the temperature of the predetermined position of the living body obtained from an estimated temperature distribution, based on the obtained CT image, the stored organism parameters, and established heating condition, thereby estimating a temperature distribution on the CT image.

In the thermotherapy apparatus according to the present invention, the temperature distribution on the CT image is estimated depending on the CT image, organism parameters, and heating conditions beforehand supplied to the apparatus. Since the temperature distribution first estimated is different from an actual temperature distribution in some cases, the apparatus modifies the distribution depending on a temperature at a point or temperatures at several points actually measured, thereby producing a temperature distribution much more similar to the actual temperature distribution.

The measured temperature is adopted to correct the estimated temperature distribution and hence need not necessarily be obtained from a position in the living body, which reduces the necessity of inserting the temperature sensor into the body of the patient. This advantageously relieves the patient from pain and prevents infectious disease from entering the body.

Moreover, since the temperature distribution can be obtained in the two-dimensional or three-dimensional region, there can be controlled, for example, the output of the high frequency power and the temperature and the circulation flow rate of the thermostatic liquid in the boluses. This improves the reliability of the thermotherapy and prevents the occurrence of undesired hot spots and burns on the body surface of the patient. Furthermore, as a result of the computer tomography image of the patient in this system, influences of the individual characteristics of the patients e.g. the body countour and the thickness of the fatty layer can be reduced.

A thermotherapy apparatus according to the present invention includes applicators each having an electrode for applying a high frequency voltage to a living body and means for generating the high frequency power to be applied between the electrodes in which the apparatus is characterized by comprising CT image acquire means for acquiring a CT image of a living body, living body parameter store means for storing therein parameters of textures and/or viscera of the living body, therapy condition report means for determining and for reporting at least one of the conditions including the size and position of the electrodes, a high frequency power, and a high frequency power application time most suitable for the therapy based on the acquired CT image, temperature distribution estimate means for estimating, based on the organism parameters stored in the store means under the therapy condition, a temperature distribution on the CT image of the body, and output means for displaying or for recording the estimated temperature distribution.

In the thermotherapy apparatus according to the present invention, there can be estimated a temperature distribution on the CT image under the established heating condition. In consequence, a therapy schedule can be prepared such that prior to an actual treatment of a patient, various therapy conditions are established to attain a temperature distribution most suitable for the treatment of the patient. Based on the treatment schedule, an effective therapy can be conducted without danger; moreover, great experience and skill are not necessary for the operator. Namely, this apparatus is advantageous in that an operator not fully versed in this field may set an optimal heating condition. In addition, the apparatus may be adopted as a model schedule device and hence experiments for a therapy may be dispensed with.

BRIEF DESCRIPTION OF THE DRAWINGS

These and other objects and advantages of the present invention will become apparent by reference to the following description and accompanying drawings wherein:

FIGS. 3 to 5 are schematic diagrams showing the configuration of a data base disposed in the thermotherapy apparatus;

DESCRIPTION OF THE PREFERRED EMBODIMENTS

Figure 1:
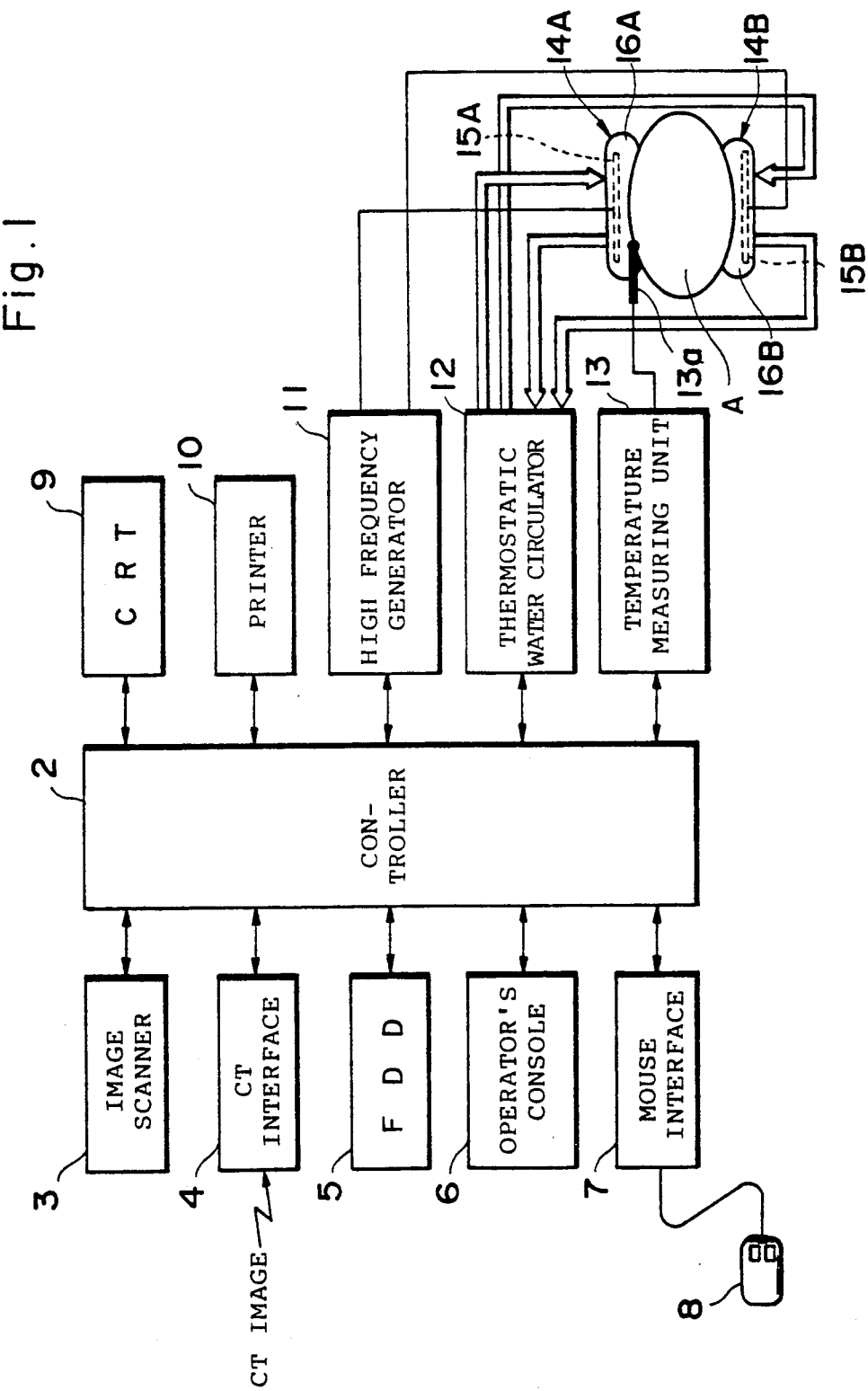
FIG. 1 is a block diagram schematically showing the constitution of a thermotherapy apparatus in an embodiment according to the present invention.

FIG. 1 is a block diagram illustratively showing a thermotherapy apparatus in an embodiment according to the present invention.

The thermotherapy apparatus of FIG. 1 includes a control unit 2 implemented e.g. with a micro computer. The controller 2 is provided with functions such as a function to acquire an image created by a computerized tomography or tomogram (CT), a function to automatically select a heating condition, a function to estimate and to modify a temperature distribution on the CT image, and a function to control a high frequency generator and a thermostatic water circulating unit.

The CT image may be produced not only by the tomogram but also by a nuclear magnetic resonance (NMR). Only if a cross section of a living body A can be correctly presented, the CT image may be drawn by a human operator. Each of the applicators 14A and 14B, which will be described later, is generally circular in shape as seen in a plan view. The cross-sectional view of a portion of an organism enclosed with a pair of applicators 14A and 14B through a cross-sectional plane passing through the center line of the applicators 14A and 14B (the highest temperature is developed in this plane) is favorably adopted as the CT image.

The CT image is supplied to the controller 2 by means of an image scanner 3, a CT interface 4, or a floppy disk driver 5. The image scanner 3 scans a CT image on a film to read in the image so as to deliver the obtained image to the control unit 2. In place of the image scanner 3, a video camera may be disposed in the configuration to read in a CT image. In any case, these methods are effective when the CT image is kept stored only on a film.

The CT interface 4 is employed to directly process data representing a CT image in an online system. That is, the CT image received is delivered via the CT interface 4 to the control unit 2.

The floppy disk driver (FDD) 5 is disposed to access a data base stored on a floppy disk and to load the flopy disk with data such as an estimated temperature distribution. In a case where the CT image data is beforehand kept stored on a floppy disk, the floppy disk driver 5 reads the data therefrom to output the obtained CT image data to the controller 2. For the storage of the data base, there may also be adopted such storing media as a hard disk and an optical disk.

The operator's console 6 including a keyboard and other constituent elements is utilized to input therefrom various kinds of commands and data. The control unit 2 is also linked with a mouse 8 via a mouse interface 7. The mouse 8 is disposed to draw graphic items on a display such as contours of textures and/or viscera and the shapes of the applicators. In place of the mouse 8, an input device such as a tablet may be employed for the identical purpose.

A cathode ray tube (CRT) 9 is adopted to display thereon information items including the acquired CT image, the estimated temperature distribution, the heating condition, the state of the thermotherapy apparatus, etc. Data items such as the temperature distribution and the heating condition are printed out on a print form by a printer 10. A liquid crystal display or the like may also be utilized in place of the CRT 9.

A high frequency generator 11 produces a high frequency voltage to be applied between electrodes 15A and 15B of the applicators 14A and 14B. The high frequency generator 11 turns on and off the application of power and changes the magnitude thereof under supervision of the controller 2.

A thermostatic water circulator 12 is disposed to circulate thermostatic water in boluses 16A and 16B of the applicators 14A and 14B, respectively. The control unit 2 also controls the temperature of the water, the flow rate thereof, and the start (on) and stop (off) of the water circulation.

A temperature measuring unit 13 comprises a temperature sensor 13a sensing a temperature $T_M$ of a living body A. The temperature $T_M$ thus measured is fed to the control unit 2 for the correction of the temperature distribution, which will be described later. Since the measured temperature $T_M$ is obtained to correct the temperature distribution, the temperature need not be necessarily obtained from an actual location in the organism, namely, the temperature of a position on a surface of the living body or the temperature of the water in the bolus 16A or 16B may be adopted. In consequence, the temperature sensor 13a need not be inserted into the body A.

Subsequently, the operation of the thermotherapy apparatus will be described by reference to the flowcharts of FIGS. 2a to 2d.

Figure 2A:
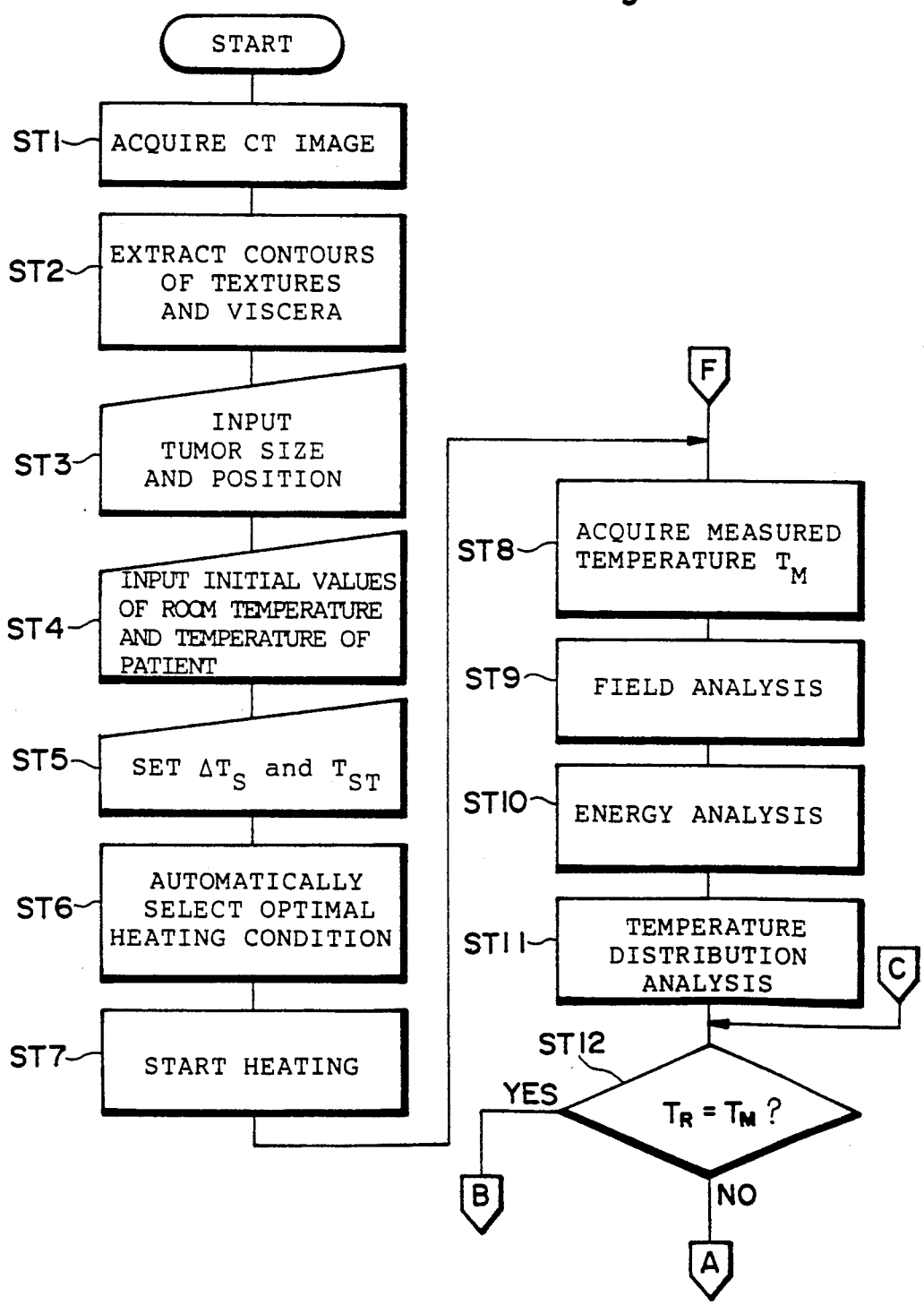
FIGS. 2a to 2d are flowcharts useful to explain the operation of the thermotherapy apparatus of FIG. 1.

Referring first to FIG. 2a, a CT image is acquired by the control unit 2 (step (ST) 1). The CT image is inputted thereto from the image scanner 3 or from a floppy disk or an online processing as described above. The controller 2 then displays the received CT image on the CRT 9.

Then, the operator draws with the mouse 8 contours of textures and internal organs on the CT image presented on the CRT 9 (ST 2). The contours of the textures and internal organs may be extracted through computer processing in an automatic manner to a certain extent based on gradation differences existing in the CT image or differences between CT values (e.g. a transmission coefficient of X rays in the case of X ray tomography) of the CT image. However, depending on the case, the computer cannot clearly discriminate the textures and viscera on the CRT 9. In consequence, it is favorable that the operator corrects with the mouse 8 the contours thereof thus automatically presented on the CT image. In any situation, the operator need only make a selection depending on conditions for the automatic contour extraction, for the correction thereof, or for the drawing of the contours by the operator.

Next, the operator draws with the mouse 8 a tumor T in the CT image presented on the CRT screen (ST 3) for the following reason. That is, in general, a tumor cannot be easily extracted by the computer from the gradation and/or CT value discrepancies obtained from the CT image.

Figure 8:
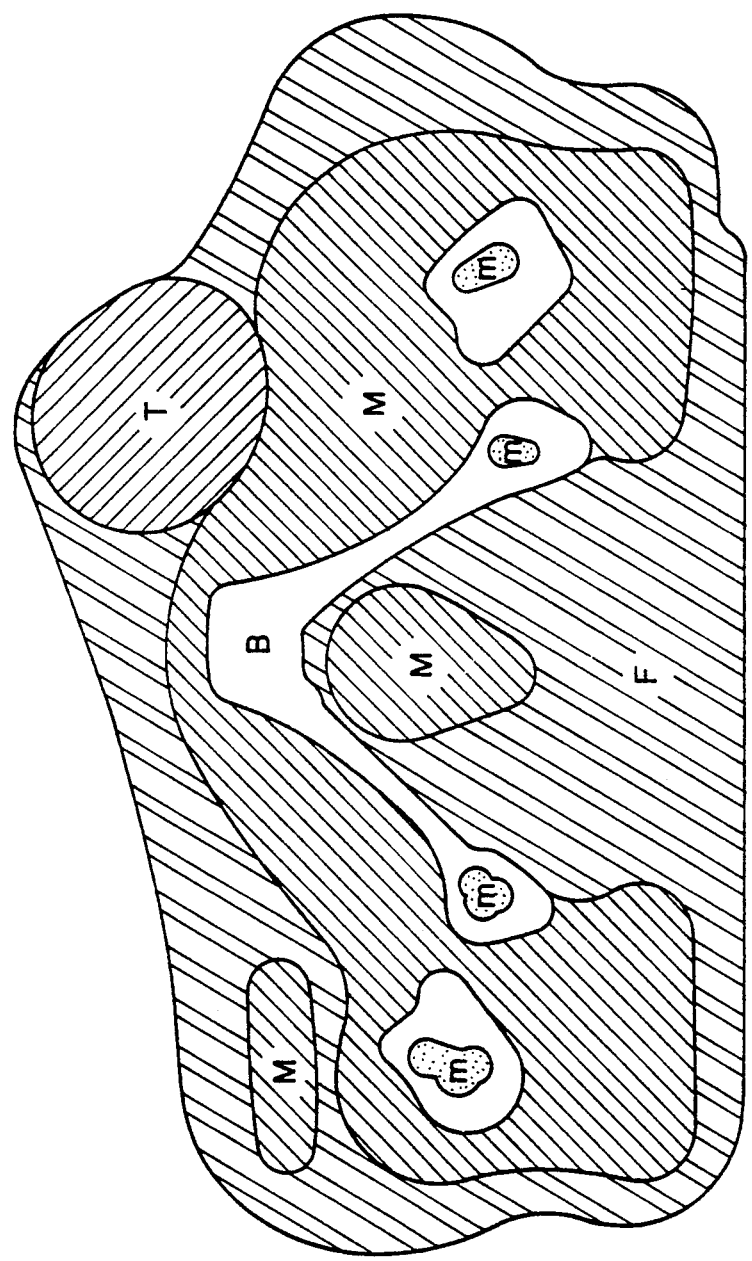
FIG. 8 is a diagram illustratively showing an example of a CT image including contours of textures and internal organs and positions and sizes of tumors.

FIG. 8 illustratively shows an example of the CRT image in which the tumor T is just drawn in a CT image including contours of textures and internal organs extracted by the computer. In this image, letters M, F, B, and m denote a muscle, a fatty portion, a bone, and a marrow of a bone, respectively.

Moreover, the operator sets a room temperature and a temperature of the human body by use of buttons and/or keys disposed in the console 6 and the mouse 8 (ST 4). Since these values are ordinarily kept retained within ranges preset for the respective values, the operator may instruct the apparatus to use default values beforehand prepared therein.

In addition, the operator inputs a setting value $\Delta T_S$ for a temperature increase rate and a target temperature $T_{ST}$ of the tumor portion (ST 5).

Figure 5:
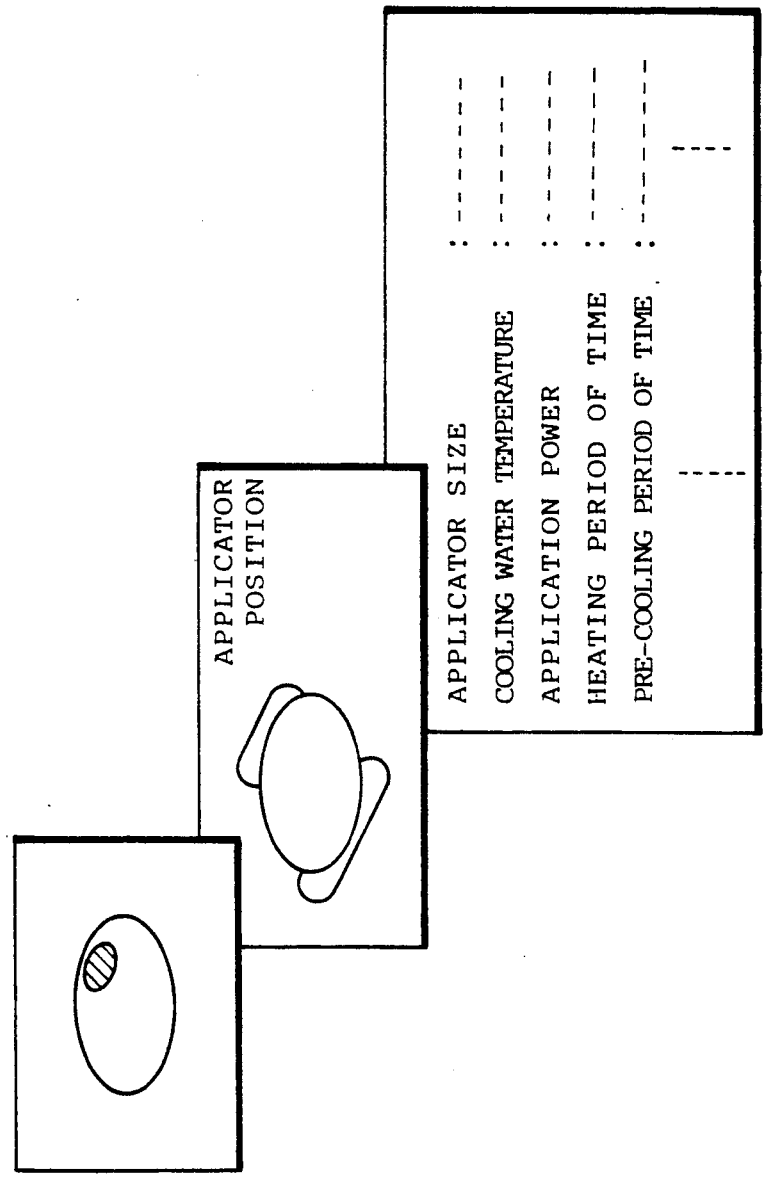

Thereafter, the apparatus automatically choses an optimal heating condition (ST 6). The heating condition presented on the CRT screen is associated with five kinds of condition elements as follows.
i) Applicator size and position
ii) Cooling water temperature
iii) Application power
iv) Heating period of time
v) Pre-cooling period of time These condition elements are automatically selected as follows. That is, the data base loaded on a floppy disk or the like contains data items respectively indicating a center position and a size of the tumor T. The apparatus selects from the data base a pair of values respectively matching or having the smallest discrepancy from the position and size of the tumor inputted in the step 3. The data items related to the tumor are also associated with such data as those of the position and size of the applicator, the cooling water temperature, etc. as shown in FIG. 5. These data items are obtained from the temperature computation beforehand achieved and are stored in a data base configuration.

Figure 4:
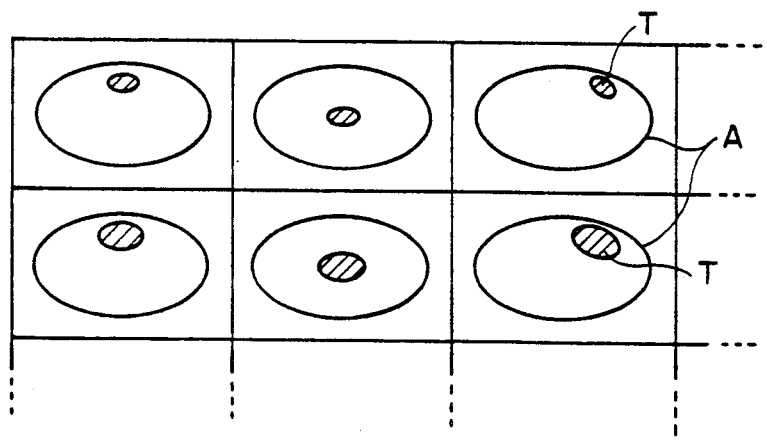
Figure 9:
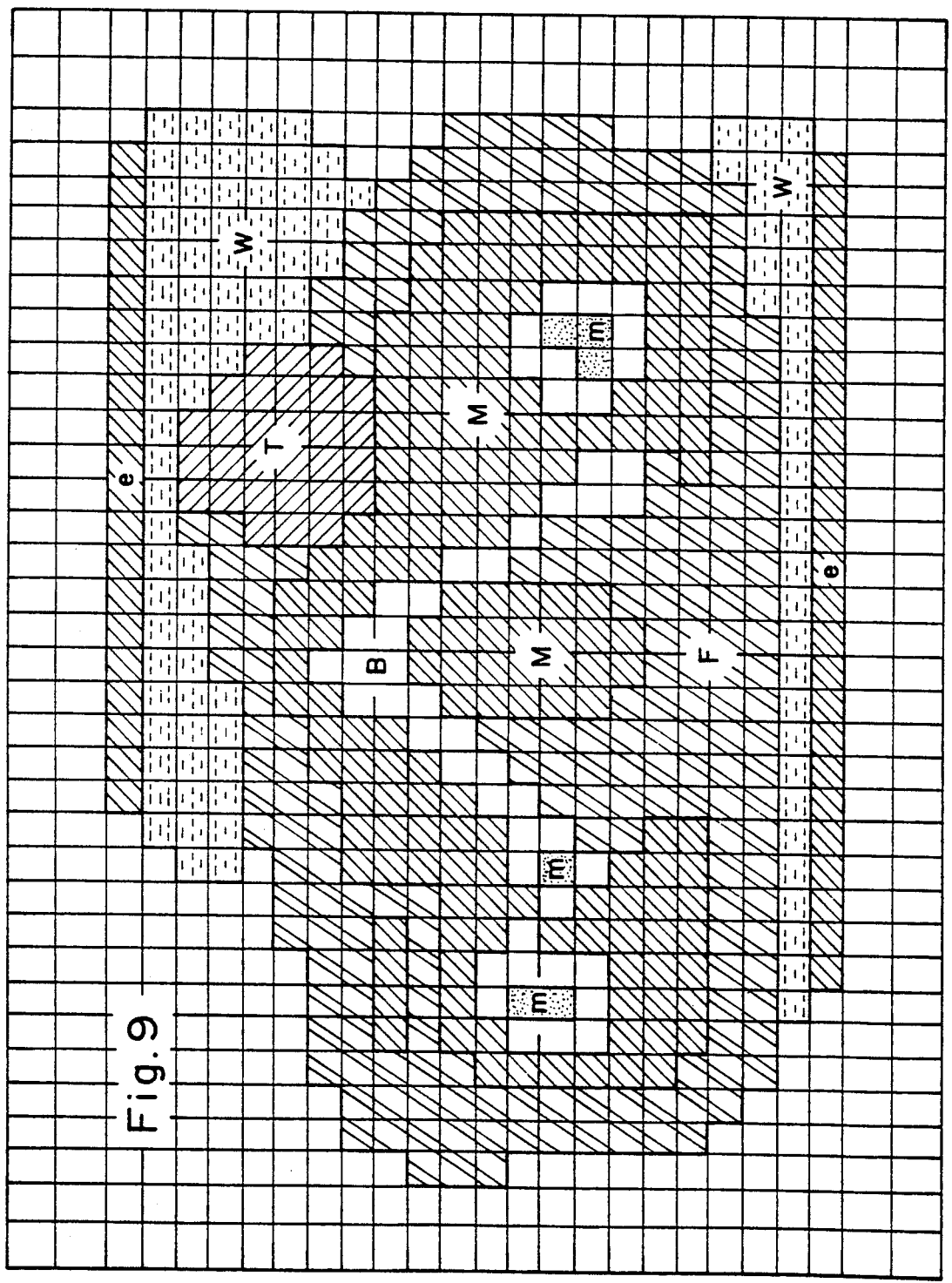
FIG. 9 is a diagram showing an example of a CT image subdivided into small areas.

The operator draws with the mouse 8 the images of the applicators in the CT image presented on the CRT 9. This is because the data of the CT image obtained by the image scanner 3 are in general different from the data stored in the data base of FIG. 4. Thereafter, the image is subdivided into quite small rectangles (or triangles) so as to produce approximated contours of the viscera, the tumor, and applicators by use of the minute areas as units for the contour approximation. FIG. 9 shows the image finally developed on the CRT 9 in which letters e and W respectively designate an electrode and a bolus (liquid bag or thermostatic water).

When the initial heating condition is determined, the operator connects the applicators specified for an objective treatment to the thermotherapy apparatus and then attaches the applicators onto the body of a patient. In the case where the applicators are configured to be automatically attached onto the body, after confirming that the applicators are linked with the thermotherapy apparatus, the apparatus sequentially moves the respective components, e.g., a supporting mechanism of the applicators to set the applicator, to a position specified by the initial heating condition, thereby attaching the applicators onto the patient.

After the applicators are thus attached onto the body, in order to adjust the water temperature the controller 2 issues an instruction such that the setting temperature of the thermostatic water circulator 12 is set to the value selected in the step 6. When the actual water temperature reaches the specified temperature, the apparatus initiates counting or measuring the pre-cooling period of time selected in advance. When the pre-cooling period of time elapses thereafter, the system gives an alarm of the condition and displays a warning message on the CRT 9. Moreover, the high frequency generator 11 applies a high frequency power selected in the step 6 between the electrodes 15A and 15B of the applicators 14A and 14B (ST 7).

When the heating operation is commenced, the controller 2 receives at an interval of time (e.g. 30 seconds) the measured temperature $T_M$ from the temperature measuring unit 13 (ST8).

The controller 2 then conducts an electric field analysis (ST 9) to obtain a potential $\phi$ for each of the minute rectangular or triangular area. Namely, the step 9 solves the following Laplace equation (1) with respect to the potential $\phi$.

$$\epsilon_x(\partial^2\phi/\partial x^2) + \epsilon_y(\partial^2\phi/\partial y^2) = 0 \quad (1)$$

where, the dielectric constant $\epsilon$(F/m) is obtained from the relative (specific) dielectric constant $\epsilon_r$ and the dielectric constant $\epsilon_0$ of vacuum. As shown in FIG. 3, the specific dielectric constant $\epsilon_r$ is beforehand loaded for each of the textures and the internal organs in the data base.

Next, an energy analysis is carried out to compute a heat or thermal energy Wh produced in each minute area (ST 10). The potential is differentiated to attain an electric field intensity E. By substituting the obtained value in the following equation, the thermal energy Wh is determined.

$$Wh = (\tfrac{1}{2})\sigma|E|^2 \quad (2)$$

where (in units of $\Omega/m$) denotes electric conductivity. The value of the conductivity is also loaded for each texture and each internal organ in the data base (FIG. 3).

Subsequently, the temperature distribution is analyzed, namely, a temperature is computed for each small area (ST 11). The apparatus solves the following bioheat transfer (BHT) equation (3).

$$\rho \cdot c \cdot \frac{\partial T_1}{\partial t} - \kappa \cdot \left( \frac{\partial^2 T_1}{\partial x^2} + \frac{\partial^2 T_1}{\partial y^2} \right) = Wh - F \cdot \rho \cdot \rho_b \cdot C_b(T_1 - T_B) \quad (3)$$

where, letters $\rho$, c, $\kappa$, and F respectively indicate for each of the textures and internal organs a volume density (kg/m³), a specific heat (J/kg °C.), a coefficient of heat transfer (W/m °C.), a blood flow rate (m³/kg·s). When necessary, the specific values of these items are obtained from the data base of FIG. 3. The blood flow rate is defined as a volume of blood flowing for each unitary period of time through a texture or an internal organ of a unit of weight. The value of the blood flow rate is in general decreased in a tumor. Moreover, $\rho_b$, $C_b$, and $T_B$ denote a volume density, a specific heat, and a temperature of the blood, respectively. In the equation (3), the first and second terms of the left side respectively designate a heat accumulated in the living body and a thermal transfer, whereas the second term of the right side represents a cooling effect owing to the blood flow.

In the processing of steps 9 to 11 of this embodiment, the analyses are carried out according to a finite element method (FEM). In addition to the finite element method, there may be adopted such analysis methods as the boundary element method (the precision of the results is slightly lower than that of the results attained in the finite element method) and difference calculus.

In step 11, when the temperature $T_i$ is obtained for each minute area, a temperature distribution is created from the obtained data to be displayed on the CRT 9 or to be printed on a print form by the printer 10. The computation of the temperature $T_i$ need not necessarily be achieved for all small areas, that is, the computation may be conducted only for the representative points including the temperature measurement points.

Thereafter, the temperature $T_i$ (to be designated as $T_R$) obtained for a minute area associated with a point where a temperature is actually measured is compared with the measured temperature $T_M$ to decide whether or not these temperature values match each other (ST 12). If this results in YES (match) or NO (mismatch), control branches to a step 24 or 13, respectively.

Figure 2B:
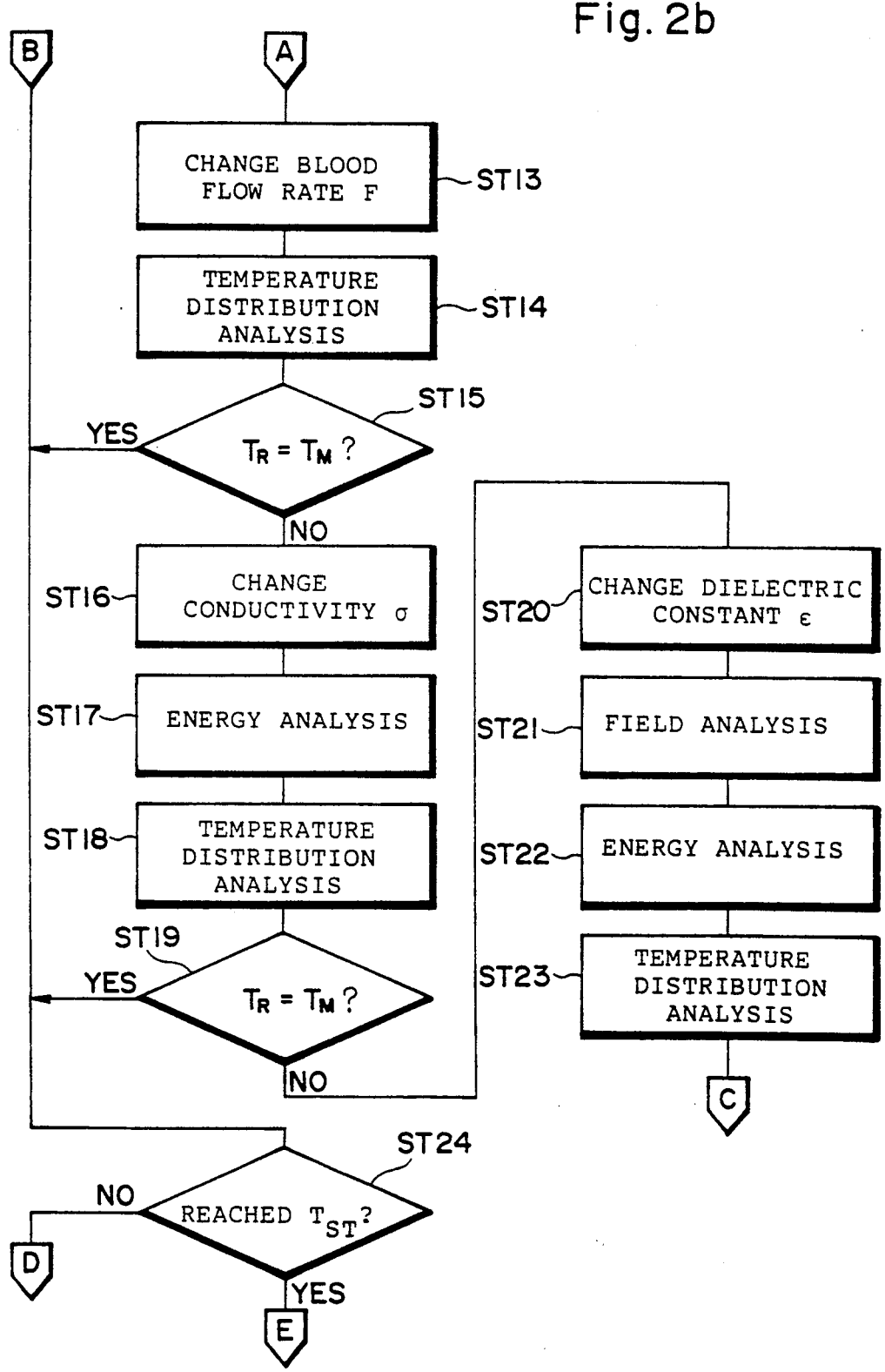

Referring now to FIG. 2b, when the computed temperature $T_i$ is different from the measured temperature $T_M$ (NO in step 12), the blood flow rate F, which is one of the coefficients (parameters), is altered (increased or decreased) in such a manner that the discrepancy $\Delta T_R = |T_R - T_M|$ approaches zero (ST 13). Thereafter, the equation (3) is solved again for the temperature distribution analysis (ST 14).

In the equation (3), the second term of the right side including the blood flow rate F indicates a heat diffusion in the living body due to the blood flow. When the blood flow rate F becomes greater, the diffusion of the produced heat is increased to suppress the increase in the temperature $T_R$. Conversely, when the blood flow rate F takes a smaller value, the suppression of the increase in the temperature $T_R$ is reduced. The value of the blood flow rate F is corrected depending on the sign (positive or negative value) of the difference $\Delta T_R$ and the magnitude of the absolute value thereof.

The system again checkes to determine whether or not the temperature $T_R$ obtained by the calculation with use of the new value of the blood flow rate F matches the measured temperature $T_M$. If this judgement results in YES or NO, the processing proceeds to step 24 or 16, respectively (ST 15). If the result is NO, control may also be returned to step 13 to change again the blood flow rate F.

In any case, when the system decides that the change only in the blood flow rate F cannot lead to a temperature distribution for which the computed temperature $T_R$ becomes identical to the measured temperature $T_M$, another parameter is selected so as to vary the value thereof.

First, the electric conductivity $\sigma$ is altered (increased or decreased) to minimize the difference $\Delta T_R$ (ST 16)

for the following reason. When the condition $T_R \neq T_M$ (or the $\Delta T_R$ is not a fixed value) results even when the blood flow rate F is changed, the temperature distribution is considered to depend on the conductivity $\sigma$ to some extent and hence causes an error in the generated thermal energy Wh.

The expression (2) is solved by using the altered conductivity $\sigma$ to attain the thermal energy Wh (ST 17). Based on the computed value of the thermal energy Wh, the expression (3) is solved to determine the temperature $T_i$ of each small rectangular or triangular region (ST 18).

The apparatus then judges to determine whether or not the temperature $T_R$ obtained with the new value of the conductivity $\sigma$ matches the measured temperature $T_M$ (ST 19). If this judgment results in a YES or NO, control is passed to step 24 or 20, respectively.

When the condition $T_R \neq T_M$ (or the $\Delta T_R$ is not a fixed value) results even when the conductivity $\sigma$ is changed, it is considered that still another parameter, e.g., the dielectric constant $\epsilon$, also influences some factors to cause an error in the potential $\phi$. Consequently, the dielectric constant $\epsilon$ is changed (ST 20) to sequentially solve the expressions (1), (2), and (3) so as to decide the temperature $T_i$ of each small area. After the processing of step 23 is completed, control again returns to step 12 for a judgement of $T_R = T_M$.

The processing steps 12 to 23 are repeatedly executed until the condition $T_R = T_M$ is obtained.

Figure 10A:
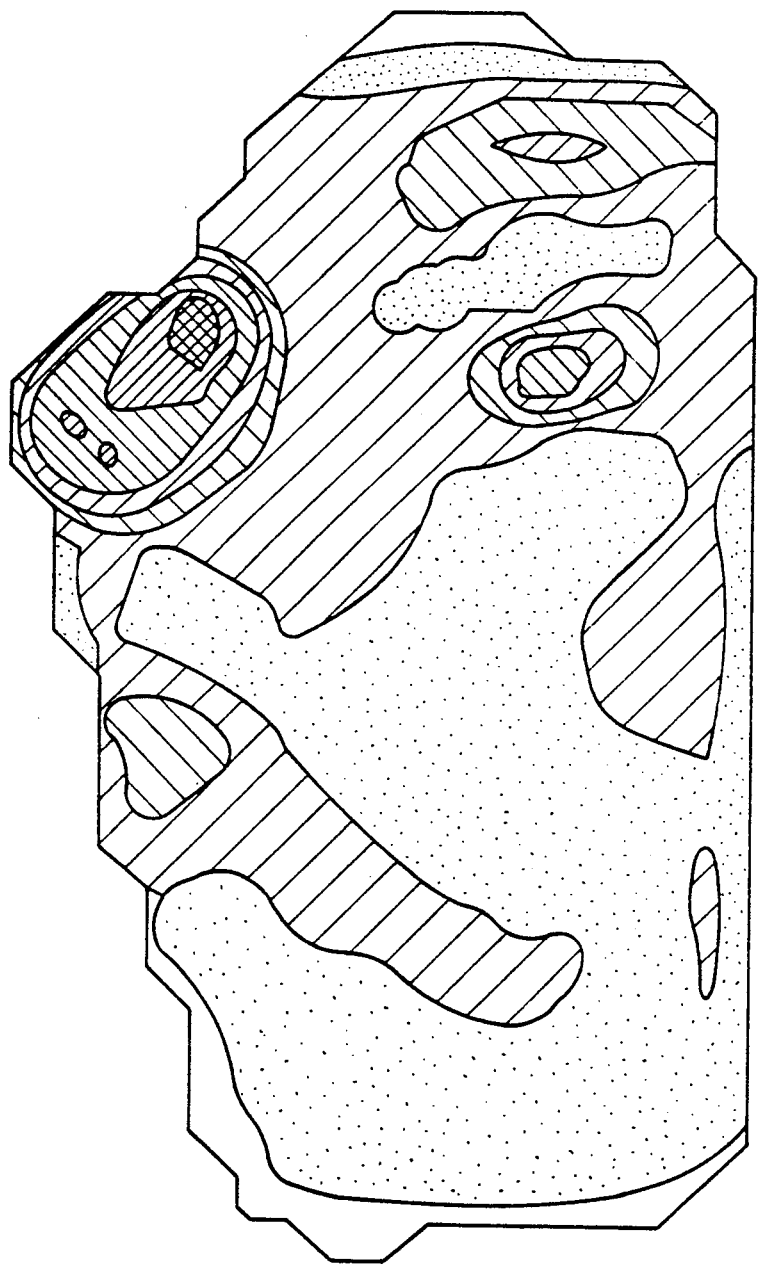
FIG. 10a is a diagram schematically showing an example of a temperature distribution estimated in the thermotherapy apparatus.
Figure 10B:
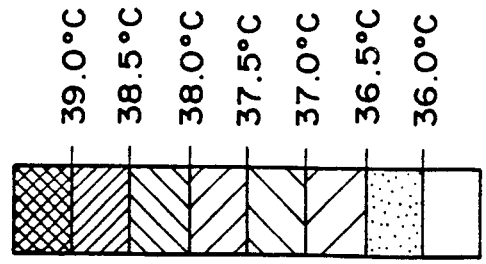
FIG. 10b is an example of a temperature range representation including patterns related to the respective temperature ranges of the temperature distribution

FIG. 10a shows an example of the temperature distribution determined as above, whereas FIG. 10b shows an example of a temperature range represention including patterns related to the respective temperature ranges of the temperature distribution. The graphic image of the temperature distribution is displayed on the CRT 9 and/or printed out on a print form by the printer 10.

In step 24, based on the temperature distribution created through the temperature distribution analysis, it is judged whether or not the temperature $T_T$ at a position where the highest temperature is developed in the tumor T reaches the target temperature $T_{ST}$ set by the operator in advance. If the judgement results in a YES or NO, the processing proceeds to step 29 or 25, respectively.

Figure 6:
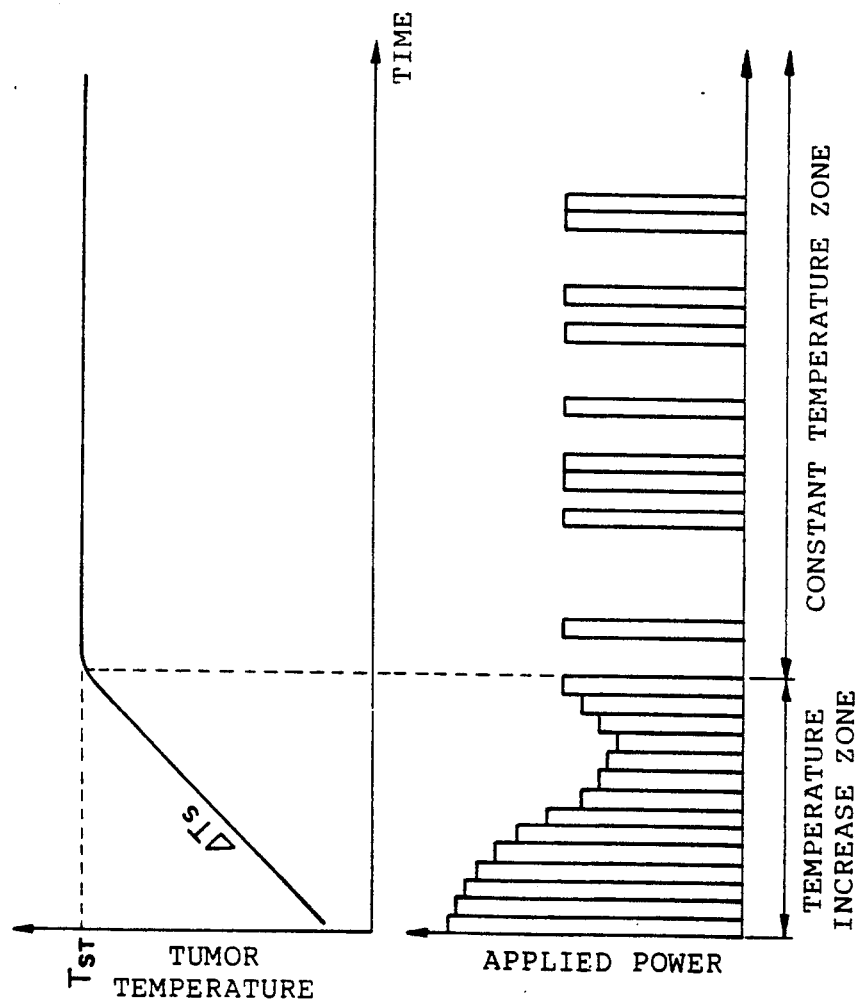
FIG. 6 is a graph showing relationships between tumor temperature and an applied high frequency power in thermotherapy.

FIG. 6 shows changes with respect to time of the temperature of the tumor T and the high frequency power applied between the electrodes 15A and 15B respectively of the applicators 14A and 14B. As can be seen from FIG. 6, the temperature of the tumor T is gradually increased up to the target temperature $T_{ST}$ so as to be kept retained at this temperature.

Figure 2C:
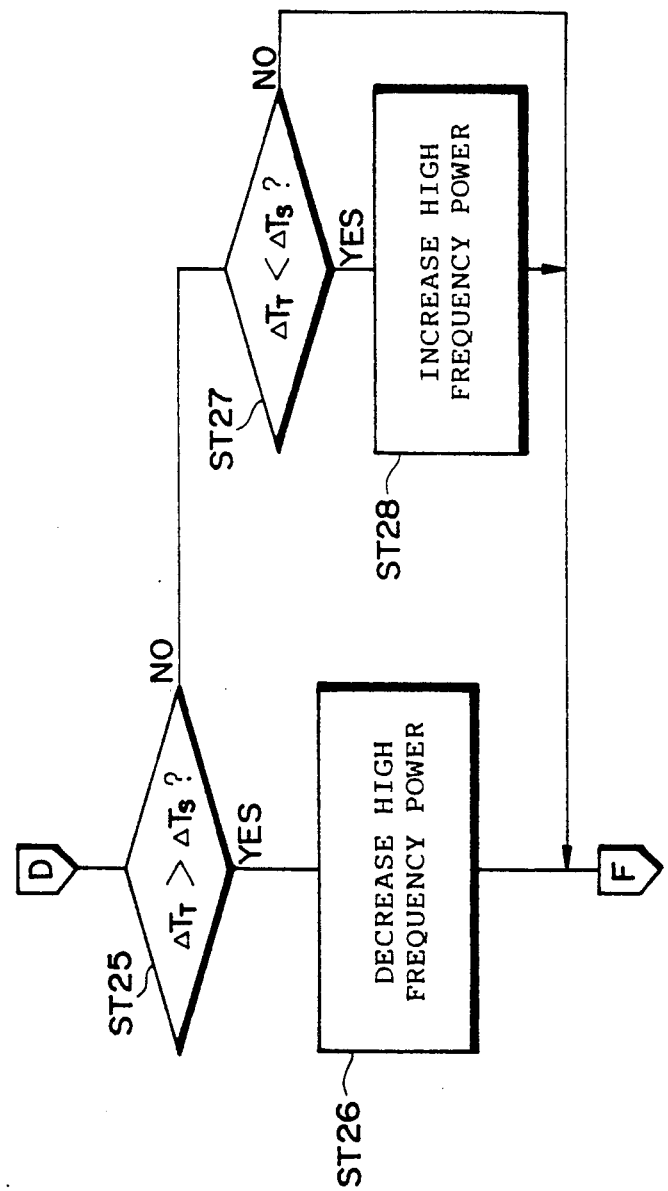
Figure 2D:
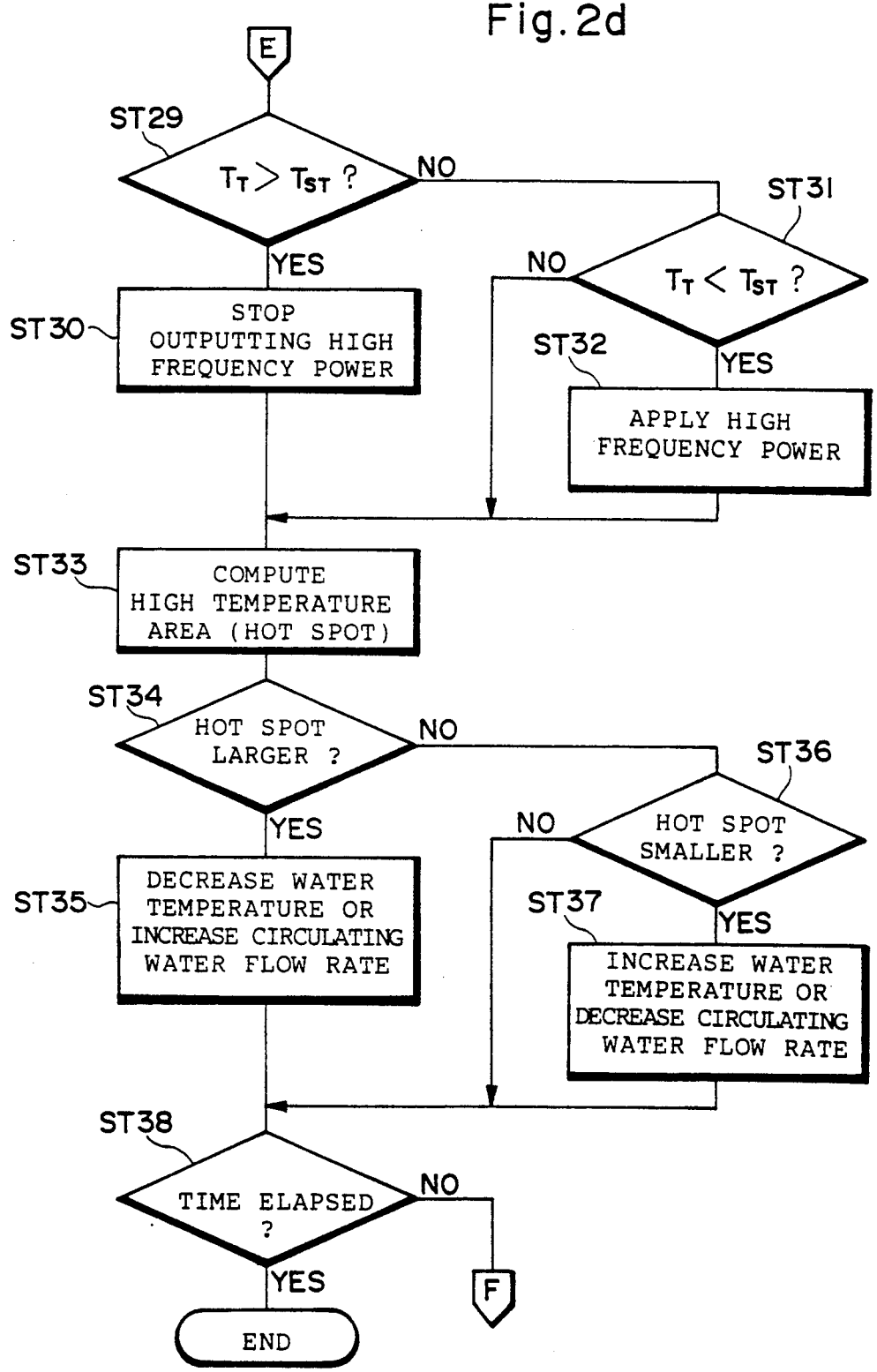

The flowchart of FIG. 2c beginning with step 25 is associated with the control of a temperature change in which the tumor temperature is increased up to the target temperature $T_{ST}$. FIG. 2d with a step 29 as the first operation is related to a control employed to keep the tumor at the target temperature $T_{ST}$, namely, in a steady state after the tumor temperature reaches the target temperature $T_{ST}$.

In the flowchart of FIG. 2c, the tumor temperature increase rate $\Delta T_T$ is regulated to be identical to the temperature increase rate $\Delta T_S$ established in advance.

The system then computes a temperature difference $\Delta T_T$ between a tumor temperature obtained in the present operation and the one developed in the previous computation preceding the present computation, for example, by 30 seconds, thereby determining whether or not the temperature discrepancy $\Delta T_T$ is larger than the temperature increase rate $\Delta T_S$ beforehand established ($\Delta T_T > \Delta T_S$; ST 25). If the judgement results in a YES, the control unit 2 instructs the high frequency generator 11 to reduce the high frequency power to be applied between the electrodes 15A and 15B (ST 26).

If step 25 ends with a result of NO, a check is made to decide whether or not the temperature difference $\Delta T_T$ is smaller than the established value $\Delta T_S$ ($\Delta T_T < \Delta T_S$; ST 27). If this is the case, the control unit 2 instructs the high frequency generator 11 to increase the high frequency power to be applied between the electrodes 15A and 15B (ST 28).

After the processing of step 26 or 28 is completed or in a case of $\Delta T_T = \Delta T_S$, control is passed to step 8 to estimate again the temperature distribution.

In the flowchart of FIG. 2d, after the tumor temperature $T_T$ once reaches the target temperature $T_{ST}$, a control operation is carried out to retain the condition $T_T = T_{ST}$.

In step 24, when the temperature of the tumor $T_T$ reaches the target temperature $T_{ST}$, the system starts counting the heating period of time.

A check is made to determine whether or not the tumor temperature $T_T$ is higher than the target temperature $T_{ST}$ ($T_T > T_{ST}$; ST 29). If the check results in a YES, the controller 2 instructs the high frequency generator 11 to stop generating the high frequency power (ST 30). Control is then transferred to step 33.

A check is made to decide whether or not the tumor temperature $T_T$ is lower than the target temperature $T_{ST}$ ($T_T < T_{ST}$; ST 31). If a YES results, the control unit 2 instructs the high frequency generator 11 to re-initiate producing the high frequency power (ST 32) and then control is passed to step 33.

For a condition $T_T = T_{ST}$, the system does not take any special action, namely, the present state concerning the high frequency power is kept unchanged.

As shown in FIG. 6, according to the embodiment, when the tumor temperature $T_T$ becomes to be identical to the preset target temperature $T_{ST}$, the high frequency generator 11 maintain the magnitude of the high frequency power developed at the moment so as to intermittently supply the power to the electrodes 15A and 15B respectively of the applicators 14A and 14B, thereby keeping the temperature steady. However, the present invention is not restricted by this embodiment, that is, the configuration and operation of the embodiment may naturally be modified or changed when necessary.

Processing steps 33 to 37 are provided to match the hot spot with the region of the tumor T, which will now be described by referring to FIGS. 7a to 7c.

Based on the computed temperature distribution, the controller 2 determines the size of the area (called a hot spot) in which the temperature already reaches the target temperature $T_{ST}$ (ST 33). Subsequently, the system judges whether or not the hot spot is larger than the region of the tumor T (ST 34). If the judgment results in a YES or NO, control is transferred to step 35 or 36, respectively.

In step 35, the controller 2 instructs the thermostatic water circulator 12 to lower the temperature of the circulating water and/or to increase the circulating water flow rate. When the processing of step 35 is finished, the processing proceeds to step 38.

Figure 7:
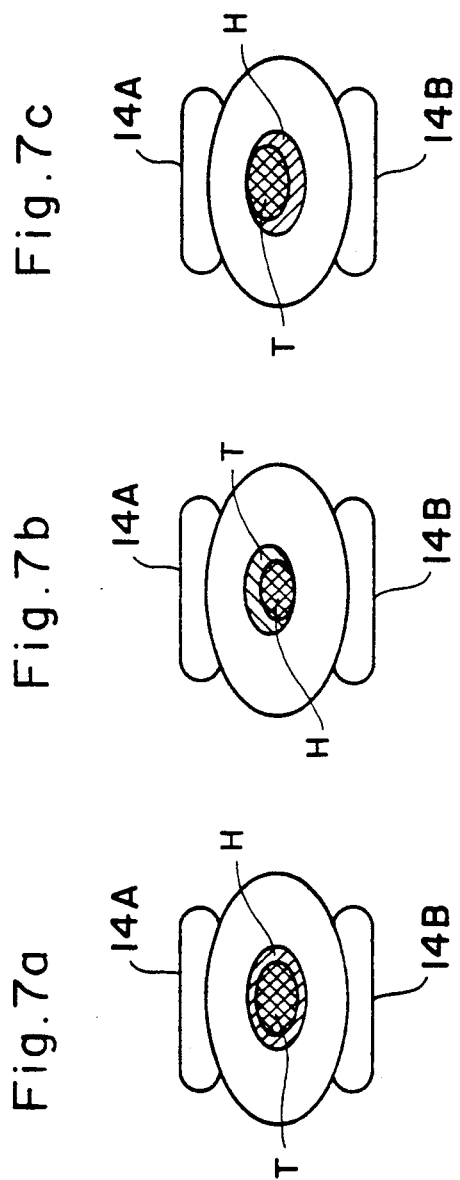
FIGS. 7a to 7c are schematic diagrams showing relationships between a hot spot and a tumor in a living body.

In each of FIGS. 7a and 7c, the hot spot H is larger than the tumor T, and hence step 34 results in a YES. In the case of FIG. 7a, the water temperature is lowered and/or the circulating water flow rate is increased for the applicators 14A and 14B. On the other hand, in the case of FIG. 7c, the hot spot H is larger than the tumor T; moreover, the hot spot H is at a position shifted toward the applicator 14B. Consequently, the temperature of the circulating water is lowered and/or the flow rate thereof is increased only for the applicator 14B.

Next, the step 36 checks to determine whether or not the hot spot H is smaller than the tumor T. If the result is a YES or NO, control is passed to step 37 or 38, respectively.

In step 37, the controller 2 instructs the thermostatic water circulator 12 to increse the temperature of the circulating water and/or to minimize the circulating water flow rate. When the processing of step 37 is completed, the processing proceeds to step 38.

In FIG. 7b, the hot spot H is smaller than the tumor T and hence step 36 results in a YES. In addition, since the position of the hot spot H is shifted toward the applicator 14B, the temperature of the circulating water is increased and/or the flow rate thereof is decreased for the applicator 14A.

In the case where the hot spot H matches with the tumor T, the system does not take any particular action.

After the processing above is completed, a check is made to determine whether or not the heating period of time preset in step ST 6 has already been elapsed (ST 38). If this is not the case, control returns to the step 8; otherwise, the system terminates the processing of the thermotherapy.

In the embodiment above, step 13 is provided to correct the blood flow rate F such that $\Delta T_R = |T_R - T_M|$ approaches zero. If the condition $T_R = T_M$ is not obtained, the correction above is required to be repetitiously accomplished.

Next, a description will be given of a variation of the embodiment in which an optimal blood flow rate F is estimated in an inverse manner.

Figure 11:
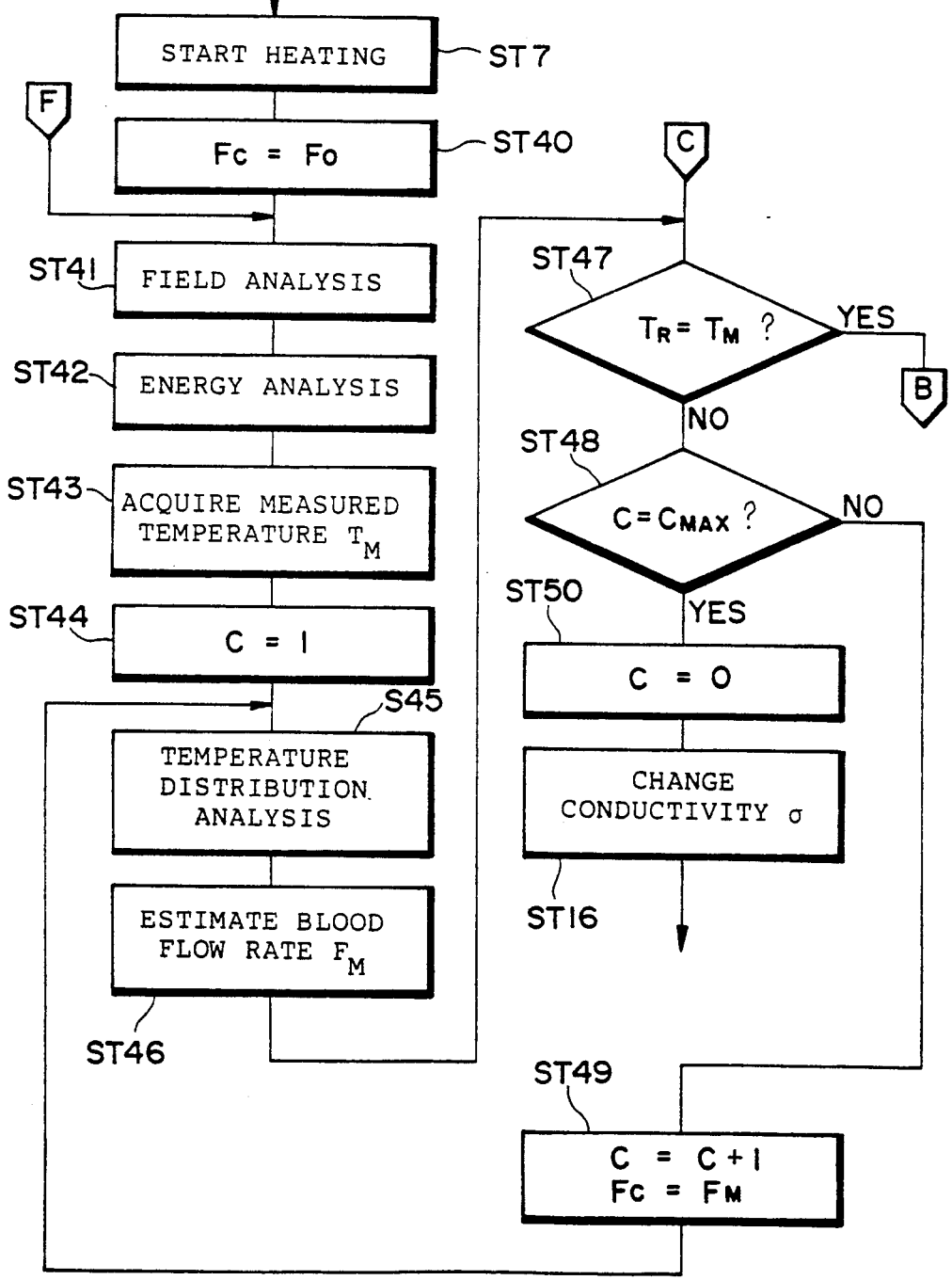
FIG. 11 is a flowchart showing a variation example of operation for a parameter correction.

FIG. 11 is a flowchart showing the operation of the blood flow rate estimation in an inverse fashion, which is to be replaced with processing steps 7 to 16 of FIGS. 2a and 2b. The remaining steps of FIGS. 2a to 2d are applicable to this example without any modification.

Figure 12:
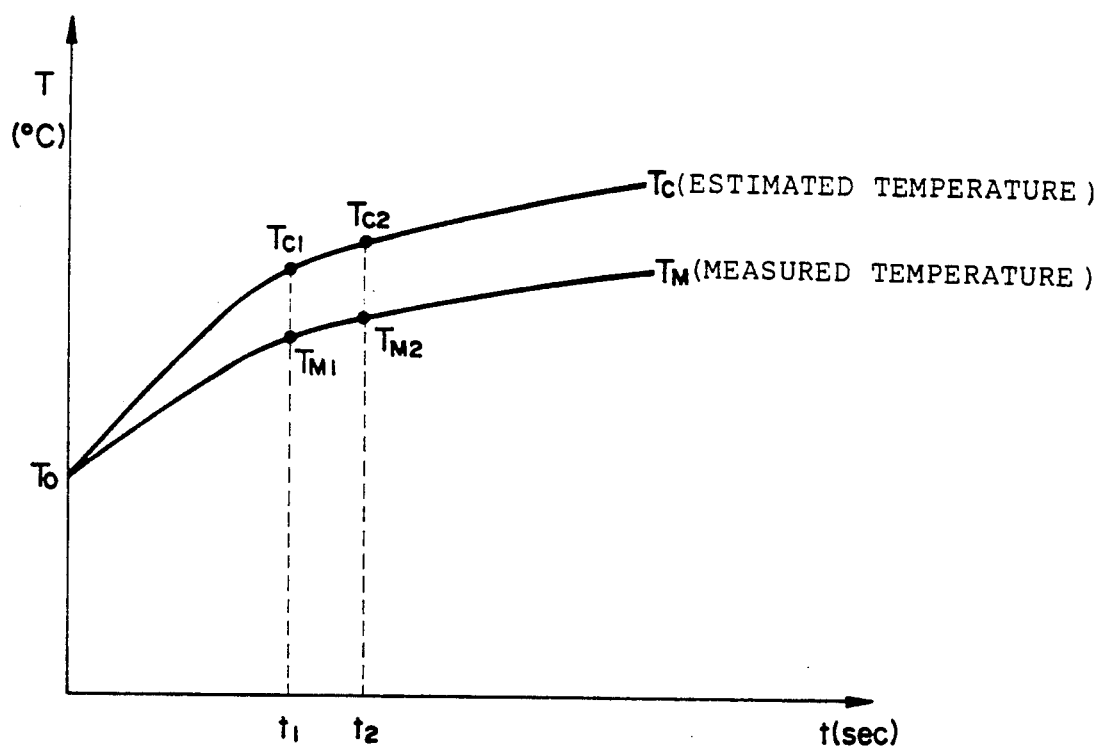
FIG. 12 is a graph showing a temperature characteristic useful to explain the principle of the parameter correction.

In the thermotherapy apparatus of FIG. 1, the estimated temperature $T_C$ (also designated as the computed temperature $T_i$ and $T_R$ (of any small area)) and the measured temperature $T_M$ vary with the lapse of time t as shown in FIG. 12. The inventors of the present invention have found that the following relationship holds between the estimated temperature $T_C$ and the measured temperature $T_M$ at two points of time $t_1$ and $t_2$ having a relatively small interval therebetween (e.g. five seconds) under a condition that the applied high frequency power is kept constant.

$$F_M = F_C \left( 1 + \frac{1}{T_{M2} - T_{M1}} \left( \frac{T_{M1} - T_{C1}}{1 - e^{-a t_1}} - \frac{T_{M2} - T_{C2}}{1 - e^{-a t_2}} \right) \right) \quad (4)$$

$$a = \frac{F_c \cdot p_b \cdot C_b}{C_t} \quad (5)$$

where, $F_C$ denotes a blood flow rate used to compute the estimated temperature $T_C$, and $F_M$ indicates a blood flow rate attained through the inverse estimation, namely, a blood flow rate which would be attained if a measurement be actually achieved.

Moreover, $C_t$ designates the specific heat of the texture or viscera undergoing the actual temperature measurement.

As shown in FIG. 12, $T_{C1}$ and $T_{C2}$ indicate estimated temperature values respectively attained at points of time $t_1$ and $t_2$; whereas $T_{M1}$ and $T_{M2}$ denote measured temperature values at points of time $t_1$ and $t_2$, respectively.

The temperature $T_C$ is estimated depending on the blood flow rate $F_C$ and then based on the expressions (4) and (5), the new blood flow rate $F_M$ is inversely estimated. The attained blood flow rate $F_M$ is used in the subsequent temperature distribution analysis.

In the flowchart of FIG. 11, when the heating operation is initiated (ST 7), an initial value $F_0$ is set to a blood flow rate $F_C$ (ST 40). The initial values $F_0$ are, for example, $5.0 \times 10^{-7}$ for a fatty layer, $8.3 \times 10^{-6}$ for a muscle, $4.2 \times 10^{-7}$ for a bone, and $5.0 \times 10^{-7}$ for a tumor.

Thereafter, using the values thus established, and while the applicators are continuously driven the system conducts an electric field analysis (ST 41) and an energy analysis (ST 42), which are respectively identical to steps 9 and 10 of FIG. 2a.

Next, the controller 2 acquires the measured temperature $T_M$ from the temperature sensor 13a (ST 43). The value of the counter C is set to one (ST 44) and then control proceeds to a temperature distribution analysis (ST 45), which is equivalent to step 11 of FIG. 2a. Namely, the equation (3) is solved to attain an estimated temperature $T_i(T_R)$. In this computation, the value $F_C$ set in the step 40 is employed as the blood flow rate F of the equation (3).

The estimation of temperature and the actual temperature measurement are respectively accomplished at least at two points of time having a small interval therebetween. Using the obtained temperature data, the inverse estimation of the blood flow rate $F_M$ is carried out according to the equation (4) in step 46.

Subsequently, the condition $T_R = T_M$, namely, whether or not $|T_R - T_M|$ is within a predetermined value range is judged (ST 47). If this results in a YES, control is passed to step 24; otherwise, the processing jumps to step 48 to decide whether or not the content of the counter C is equal to a preset value $C_{MAX}$.

Initially, step 48 results in a NO and hence control branches to step 49, which then increments the content of the counter C by one and sets $F_M$ attained by the inverse estimation of step 46 to $F_C$ (ST 49), thereby returning control to step 45.

The temperature distribution analysis is accomplished again based on the new blood flow rate $F_C$ (ST 45). Using the new value of $F_C$ and the estimated and measured temperature values, the equation (4) is again solved to inversely estimate the blood flow rate $F_M$ (ST 46).

Processing steps 45 to 49 are repeatedly carried out until the condition $T_R = T_M$ is satisfied (ST 47) or the content of the counter C becomes $C_{MAX}$ e.g. =4 (ST 48). In the interation above, when the estimated temperature $T_R$ is equal to the measured temperature $T_M$ (ST 47), control is transferred to step 24. Moreover, if the condition $C = C_{MAX}$ is obtained before the temperature matching takes place (ST 48), the counter C is reset to zero (ST 50) and then processing is returned to step 16.

According to the method of the embodiment as described above, based on time series data of measured temperature obtained from an objective portion of a patient through the heating operation in a clinical treatment, the parameter values of textures of the living body and temperature dependence characteristics thereof are repeatedly estimated in such a fashion that the data of measured temperature satisfactorily match in a sequence of time with analysis results developed from the temperature distribution analysis routine analyzing temperatures in the living body. In other words, for the objective portion, a temperature measured at an arbitrary point of time is compared with an analysis result associated therewith. If these two values match with each other within a preset error range, the value employed in the analysis as a parameter value of a texture of the living body is assumed to have been appropriately estimated. Consequently, in the processing procedure, control directly returns to the temperature distribution analysis routine to achieve a computation of a temperature distribution in a state developed after a preset period of time is elapsed. If there exists any portion of the patient for which the estimated and measured temperatures do not match with each other in the sense described above, corrections are made on the parameter values of the related textures of the living body. For example, the parameter correction of the blood flow rate is executed as described above. Thereafter, control returns to the temperature distribution analysis routine to conduct again the computations for the electric field, the thermal energy, and the temperature distribution.

Figure 13:
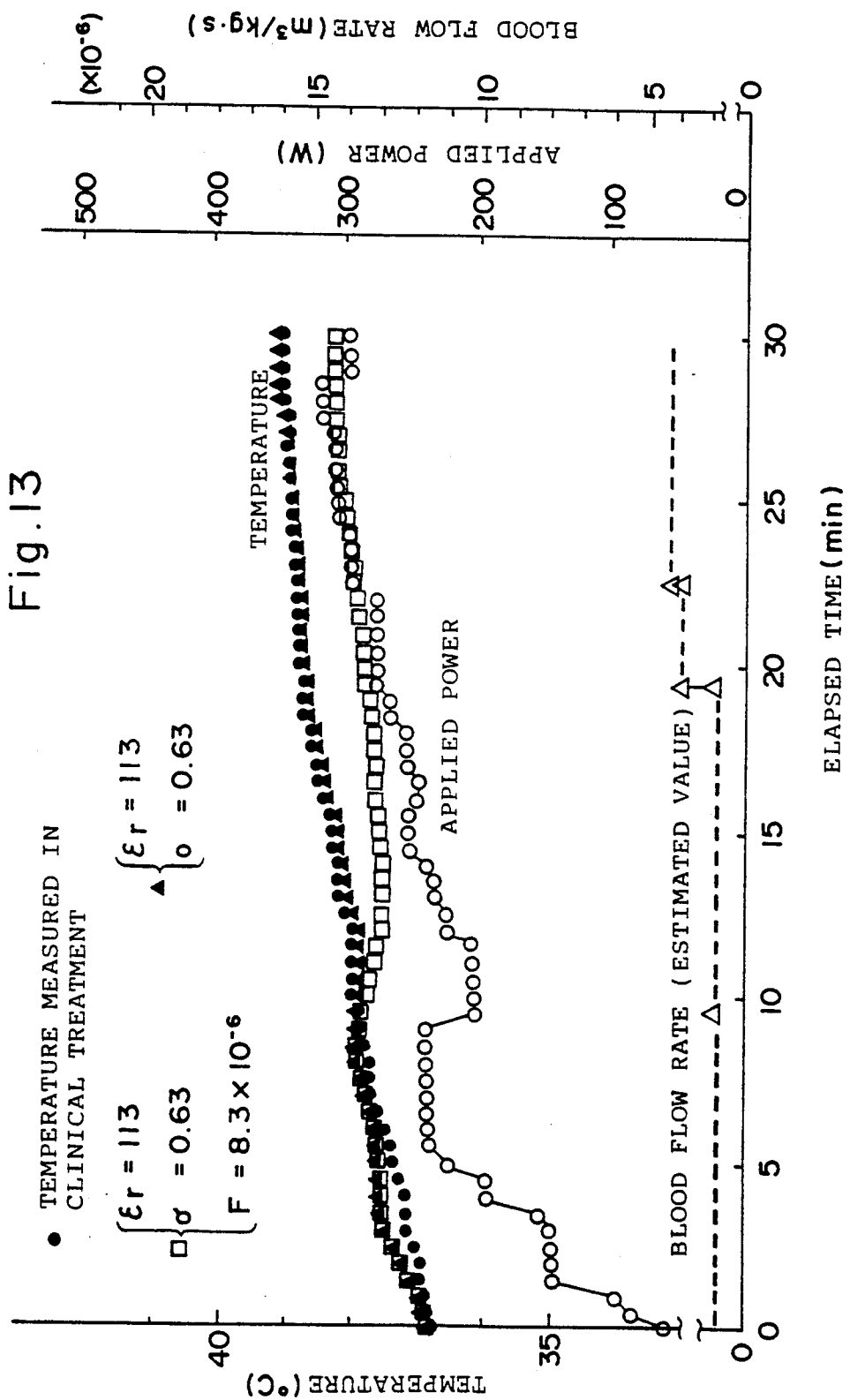
FIG. 13 is a graph showing relationships between a measured temperature and an estimated temperature with a lapse of time in a clinical treatment.

When the temperature distribution is estimated in association with the inverse estimation of the blood flow rate as described in conjunction with the embodiment, the values of measured temperature ( ) substantially match those of the estimated temperature ( ) as shown in the graph of FIG. 13. Namely, the precision of the estimated temperature is increased and hence the discrepancies in personal characteristics between the patients can be absorbed, which advantageously leads to an adaptive temperature distribution estimation. Moreover, when the inverse estimation method is applied to other parameters of a living body to configure a data base system of the respective parameters, which may possibly enable the apparatus to be applied to judgment of the state of a tumor and diagnosis of cancer.

FIG. 13 is a graph representing clinical data obtained from a muscle of a living body. In this graph,      denotes a measured temperature,      denotes a temperature obtained by the temperature distribution estimation including the inverse estimation of the blood flow rate according to FIG. 11, Δ designates a blood flow rate inversely estimated through the temperature distribution estimation, and ◯ indicates an applied power used in the apparatus.

Moreover, □ denotes a value of temperature, which is obtained from the temperature distribution estimation according to FIGS. 2a and 2b with the blood flow rate kept unchanged.

The present invention is applicable not only to high frequency thermotherapy apparatus but also to ultrasonic thermotherapy apparatus and the like.

Figure 14:
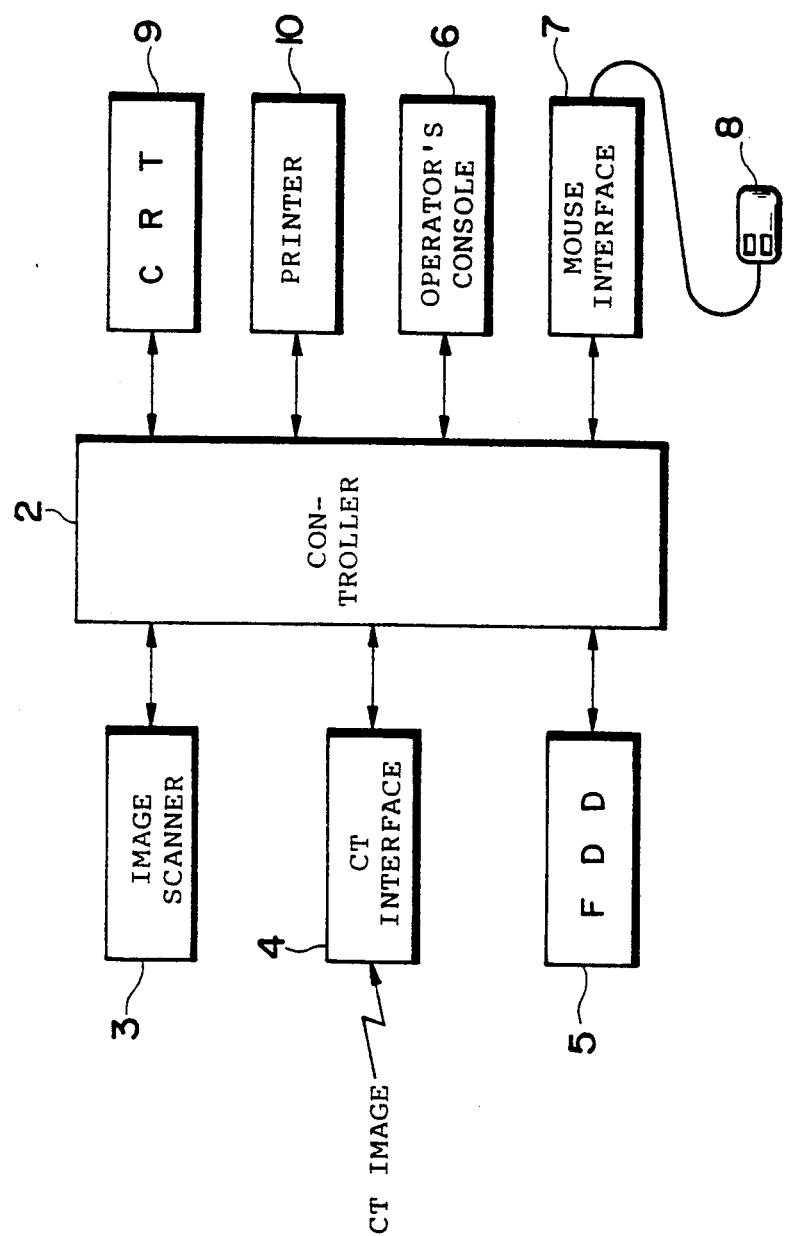
FIG. 14 is a block diagram schematically showing the configuration of a thermotherapy apparatus or a thermotherapy schedule support apparatus in an alternative embodiment according to the present invention.
Figure 15:
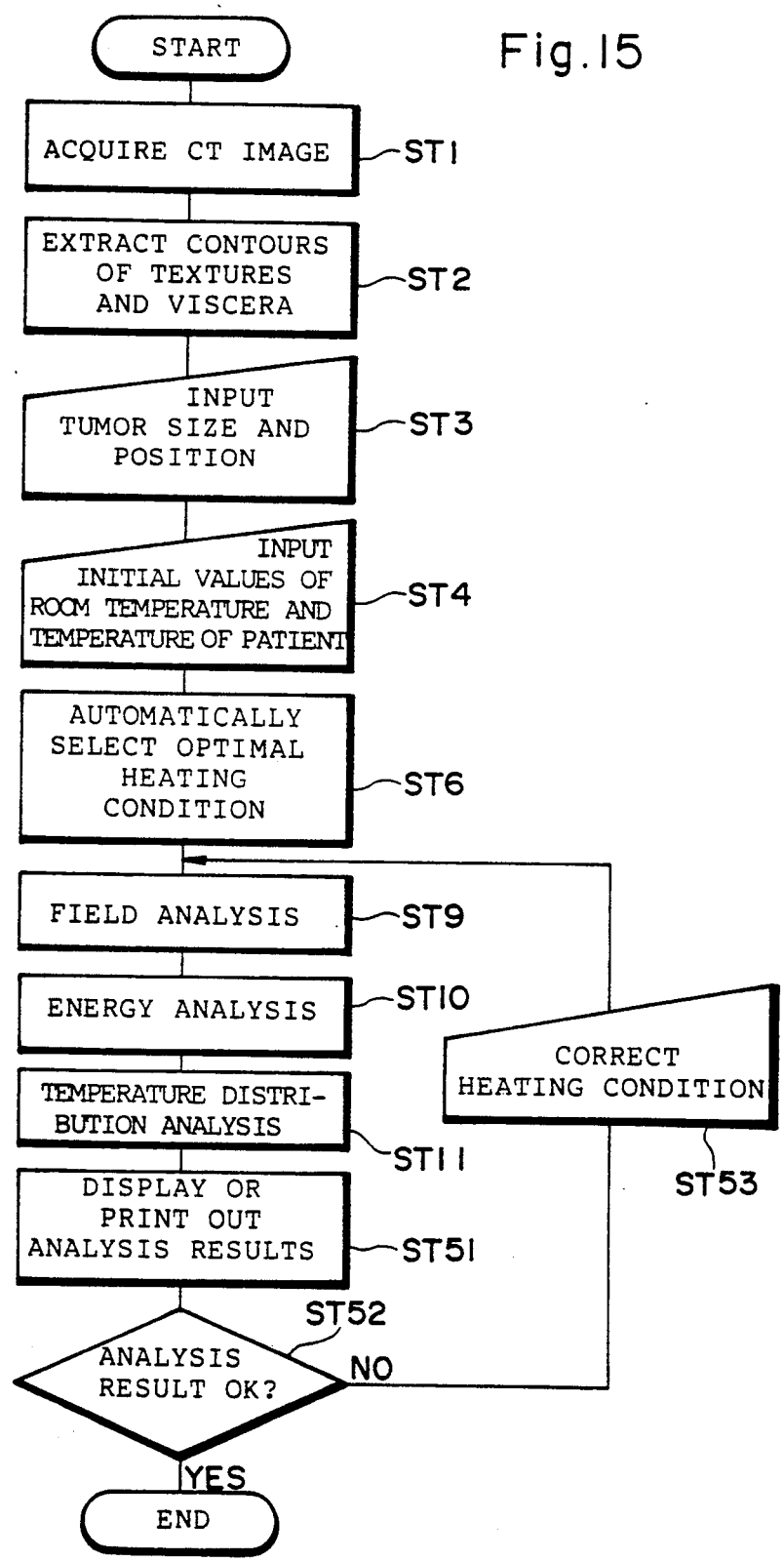
FIG. 15 is a flowchart showing a portion of the operation achieved by the apparatus of FIG. 14.

FIGS. 14 and 15 are respectively a block diagram and a processing flowchart useful to explain an embodiment of a thermotherapy apparatus having a thermotherapy schedule support function or a thermotherapy schedule support apparatus according to the present invention. In FIGS. 14 and 15, the same blocks and processing steps as those of FIG. 1 and FIG. 2a are assigned with the same reference numrals and a redundant explanation thereof will be avoided. Furthermore, in the block diagram of FIG. 14, the high frequency generator, the high-temperature water circulator, and the temperature measuring unit are omitted for simplicity.

According to this embodiment, the apparatus conducts substantially the same processing steps as those of the embodiment described above to accomplish the acqustion of a CT image, extraction of contours of textures and viscera of an organism, and input operations to get the tumor size and position as well as initial values of the room temperature and the temperature of a patient. Thereafter, the system automatically selects an optimal heating condition to carry out a field analysis, an energy analysis, and a temperature distribution analysis (ST 1 to ST 6 and ST 9 to ST 11).

The temperature values $T_i$ thus obtained for the respective minute rectangular or triangular areas are processed so as to create a temperature distribution. The temperature distribution image is then graphically presented on the CRT 9 and/or printed out on a print form by the printer 10 as shown in FIG. 10a (ST 51).

The operator then visually checks the presented or printed distribution image to determine whether or not a desired temperature distribution has been attained (ST 52). If this check results in a YES, the processing is terminated. Namely, an optimal heating condition has been determined by the operation and hence is to be employed in an actual treatment of the patient.

On the other hand, if the judgement of step 52 ends with a NO, control is passed to step 53, which instructs the operator to correct the heating condition. After the heating condition is modified, processing steps 9 to 11 and processing step 51 are executed to generate a temperature distribution under the obtained heating condition. The resultant temperature distribution is displayed on the CRT 9 and/or printed on a print form by the printer 10. Processing steps 9 to 11 and processing step 51 are repeatedly executed until the desired temperature distribution is produced.

As above, according to the present invention, a temperature distribution can be estimated on a cross-sectional plane of a CT image under the preset heating condition. In consequence, prior to an actual treatment of a patient, a thermotherapy schedule can be prepared in such a manner that an optimal temperature distribution is obtained by setting various heating conditions. Based on the treatment schedule, the thermotherapy can be efficiently achieved in safety; moreover, the operation of the thermotherapy apparatus may possibly be conducted by an operator who has not been fully experienced in this field.

What is claimed is:

1. A thermotherapy apparatus including applicators each having an electrode for applying high frequency power to a living body, each applicator comprising a bolus for cooling a surface of the living body and thermostatic liquid circulation means for circulating a thermostatic liquid in said bolus, high frequency power generating means for generating high frequency power applied to said electrodes, temperature measuring means for measuring a temperature of a predetermined position of the living body, and heating condition setting means for setting a heating condition, said thermotherapy apparatus further comprising:
means for acquiring a cross-sectional image of the living body;
means for storing parameters of textures or viscera of the living body;

temperature distribution estimation means for repeatedly correcting values of the stored parameters of the living body to minimize, based on the acquired cross-sectional image, the stored parameters of the living body and a preset heating condition, a discrepancy between a temperature repeatedly measured at the predetermined position of the living body by said temperature measuring means and a temperature of the predetermined position of the living body obtained from an estimated temperature distribution, thereby estimating a temperature distribution on the cross-sectional image;

means for setting a tumor area on the cross-sectional image as an object of thermotherapy;

means for attaining, based on the estimated temperature distribution, a hot spot having a temperature exceeding a predetermined temperature;

output control means for applying the high frequency power to said electrodes when a maximum temperature of the tumor area is less than a preset control temperature and for decreasing the high frequency power applied to said electrodes when the maximum temperature of the tumor area is not less than the preset control temperature; and thermostatic liquid control means for decreasing a temperature of the thermostatic liquid circulating in the bolus or increasing a flow rate of the thermostatic liquid circulating in the bolus when the hot spot is larger in size than the tumor area and for increasing the temperature of the thermostatic liquid circulating in the bolus or decreasing the flow rate of the thermostatic liquid circulating in the bolus when the hot spot is smaller in size than the tumor area.

2. A thermotherapy apparatus in accordance with claim 1 further including output control means for controlling an output from said high frequency power generation means based on a temperature of a pre-specified area in the living body estimated by said temperature distribution estimation means.

3. A thermotherapy apparatus in accordance with claim 1 further including:

means for beforehand storing therein a plurality of preset heating conditions; and means for selecting from the plural heating conditions stored in said storing means a heating condition suitable for the acquired cross-sectional image and the preset tumor area.

4. A thermotherapy apparatus including applicators each having an electrode for applying high frequency power to a living body, high frequency power generating means for generating high frequency power applied to said electrodes, temperature measuring means for measuring a temperature of a predetermined position of the living body, and heating condition setting means for setting a heating condition, said thermotherapy apparatus further comprising:

means for acquiring a cross-sectional image of the living body;

means for storing parameters of textures or viscera of the living body;

temperature distribution estimation means for repeatedly correcting values of the parameters of the living body to minimize, based on the acquired cross-sectional image, the stored parameters of the living body and a preset heating condition, a discrepancy between a temperature repeatedly measured at the predetermined position of the living body by said temperature measuring means and a temperature of the predetermined position of the living body obtained from an estimated temperature distribution, thereby estimating a temperature distribution on the cross-sectional image; and parameter estimations means for estimation at least one of the parameters of the living body as the applicators are continuously driven based on the parameters of the living body employed to estimate the temperature distribution, the estimated temperature determined by the temperature distribution estimation means and the measured temperature of the living body, said parameter estimation means repeatedly estimation to correct at least one of the parameters of the living body used by said temperature estimation means.

5. A thermotherapy apparatus in accordance with claim 4 further including output control means for controlling an output from said high frequency power generation means based on a temperature of a pre-specified area in the living body estimated by said temperature distribution estimation means.

6. A thermotherapy apparatus in accordance with claim 4 wherein each said applicator includes:

a bolus for cooling a surface of the living body; and thermostatic liquid circulation means for circulating a thermostatic liquid in said bolus.

7. A thermotherapy apparatus in accordance with claim 6 further including thermostatic liquid control means for controlling, based on a temperature distribution of a pre-specified area in the living body estimated by said temperature distribution estimate means, at least either one of a temperature and a circulating flow rate of the thermostatic liquid circulated by said thermostatic circulate means.

8. A thermotherapy apparatus in accordance with claim 4 further including:

means for setting a tumor area as an object of a thermotherapy on the cross-sectional image;

means for beforehand storing therein a plurality of preset heating conditions; and means for selecting from the plural heating conditions stored in said store means a heating condition suitable for the acquired cross-sectional image and the preset tumor area.

9. A thermotherapy apparatus in accordance with claim 6, further comprising:

means for setting a tumor area on the cross-sectional image as an object of thermotherapy;

means for attaining, based on the estimated temperature distribution, a hot spot having a temperature exceeding a predetermined temperature;

output control means for applying the high frequency power to said electrodes when a maximum temperature of the tumor area is less than a preset control temperature and for decreasing the high frequency power applied to said electrodes when the maximum temperature of the tumor area is not less than the preset control temperature; and thermostatic liquid control means for decreasing a temperature of the thermostatic liquid circulating in the bolus or increasing a flow rate of the thermostatic liquid circulating in the bolus when the hot spot is larger in size than the tumor area and for increasing the temperature of the thermostatic liquid circulating in the bolus or decreasing the flow rate of the thermostatic liquid circulating in the bolus when the hot spot is smaller in size than the tumor area.

10. A thermotherapy apparatus including applicators each having an electrode for applying high frequency power to a living body, and high frequency power generating means for generating high frequency power applied to said electrodes, comprising:
- means for acquiring a cross-sectional image of the living body;
- means for storing parameters of textures or viscera of the living body;
- treatment condition reporting means for determining and for reporting, based on the acquired cross-sectional image, at least one optimal condition selected from the group of conditions including a size and a position of each electrode, the amount of high frequency power applied to each electrode, and a power application period of time;
- temperature distribution estimation means for estimating a temperature distribution on the cross-sectional image of the living body based on the stored parameters of the living body under the condition reported by the treatment condition reporting means; and
- output means for displaying or for recording the estimated temperature distribution.

11. A thermotherapy apparatus in accordance with claim 10 wherein each said applicator includes a bolus for cooling a surface of the living body, and wherein the apparatus further includes thermostatic liquid circulation means for circulating a thermostatic liquid in said bolus.

12. A thermotherapy appartus in accordance with claim 11 wherein said treatment condition reporting means reports as the optimal treatment condition at least a temperature of the thermostatic liquid in each said bolus and a pre-cooling period of time thereof.

13. A thermotherapy schedule support apparatus comprising:
- means for inputting thereto a cross-sectional image of a living body;
- means for discriminating boundaries between different textures of the living body in the inputted cross-sectional image;
- store means for beforehand storing therein parameters of the living body respectively related to a plurality of textures of the living body; and
- temperature estimate means for estimating in association with the inputted cross-sectional image, with use of an intensity of an electric field applied to the living body and the parameters stored in said storing means, a temperature distribution of the living body generated due to the electric field applied thereto.

14. A therapy schedule support apparatus in accordance with claim 13 wherein said discriminating means performs an image processing on the inputted cross-sectional image to extract contours of the textures of the living body.

15. A therapy schedule support apparatus in accordance with claim 13 wherein said discriminating means includes means for inputting thereto data representing contours of the textures of the living body.

16. A therapy schedule support apparatus in accordance with claim 13 further including:
- means for measuring a temperature of a predetermined position of the living body; and
- means for correcting the parameters of the living body based on a difference between a temperature measured by said measuring means and a temperature estimated by said estimate means.

17. A therapy schedule support apparatus in accordance with claim 16, wherein said correcting means corrects the parameters of the living body such that the difference between the measured and estimated temperatures is decreased.

18. A therapy schedule support apparatus in accordance with claim 17 wherein said correcting means estimates parameters of the living body based on the parameters of the living body employed by said estimate means and the measured and estimated temperatures associated with at least two points of time.

19. A method of producing a distribution of temperature of a living body comprising the following steps of:
- attaining data representing a cross-sectional image of a living body;
- discriminating boundaries of different textures of the living body in the cross-sectional image; and
- estimating in association with the attained cross-sectional image, based on an intensity of an electric field applied to the living body and parameters of the living body respectively preset for the textures, a temperature distribution of the living body generated due to the electric field applied thereto.

20. A method in accordance with claim 19 wherein said step of discriminating the boundaries includes a step of conducting an image processing on the cross-sectional image to extract contours of the textures.

21. A method in accordance with claim 19 wherein said step of discriminating the boundaries includes a step of inputting data representing contours of the textures.

22. A method in accordance with claim 19 further including the steps of:
- measuring a temperature of a predetermined position of the living body; and
- correcting the parameters of the living body based on a temperature actually measured and an estimated temperature.

23. A method according to claim 22 wherein said step of correcting the parameters of the living body is achieved such that a difference between the measured and estimated temperatures is minimized.

24. A method according to claim 23 wherein said step of correcting the parameters of the living body is conducted depending on the parameters of the living body employed by said temperature distribution estimation step and the measured and estimated temperatures associated with at least two points of time.

* * * * *